United States Patent [19]

Matsumoto

[11] Patent Number: 4,991,442
[45] Date of Patent: Feb. 12, 1991

[54] METHOD AND APPARATUS FOR DETECTING CRACKS IN BEARINGS

[75] Inventor: Youichi Matsumoto, Yokohama, Japan

[73] Assignee: Nippon Seiko Kabushiki Kaisha, Tokyo, Japan

[21] Appl. No.: 451,013

[22] Filed: Dec. 14, 1989

[30] Foreign Application Priority Data

Dec. 16, 1988 [JP] Japan ................. 63-318011
May 25, 1989 [JP] Japan ................. 1-132130

[51] Int. Cl.⁵ .......................................... G01M 13/04
[52] U.S. Cl. .......................................... 73/660
[58] Field of Search ............ 73/118.1, 660; 364/508; 384/448; 340/682

[56] References Cited

U.S. PATENT DOCUMENTS 4,729,239 3/1988 Gordon ................. 73/660 X

Primary Examiner—Jerry W. Myracle
Attorney, Agent, or Firm—Charles S. McGuire

[57] ABSTRACT

A method and an apparatus for detecting a crack in a bearing including a stationary element, a moving element, and a plurality of rolling elements disposed between the stationary element and the moving element. A crack sensor detects a signal characteristic of a crack in the bearing. A rolling element position sensor detects a position of the rolling elements. A moving element position sensor detects a position of the moving element. When an output signal from the crack sensor is supplied for the first time, based on at least one of position signals respectively supplied from the rolling element position sensor and the moving element position sensor, there is determined a condition of the at least one of position signals to be satisfied when the output signal from the crack sensor is supplied the next time. The at least one of position signals is monitored thereafter to accumulate the output signal from the crack sensor if the output signal is supplied when the at least one of position signals satisfying the condition is supplied, to thereby determine whether or not the crack exists in the bearing based on a result of the accumulation.

18 Claims, 12 Drawing Sheets

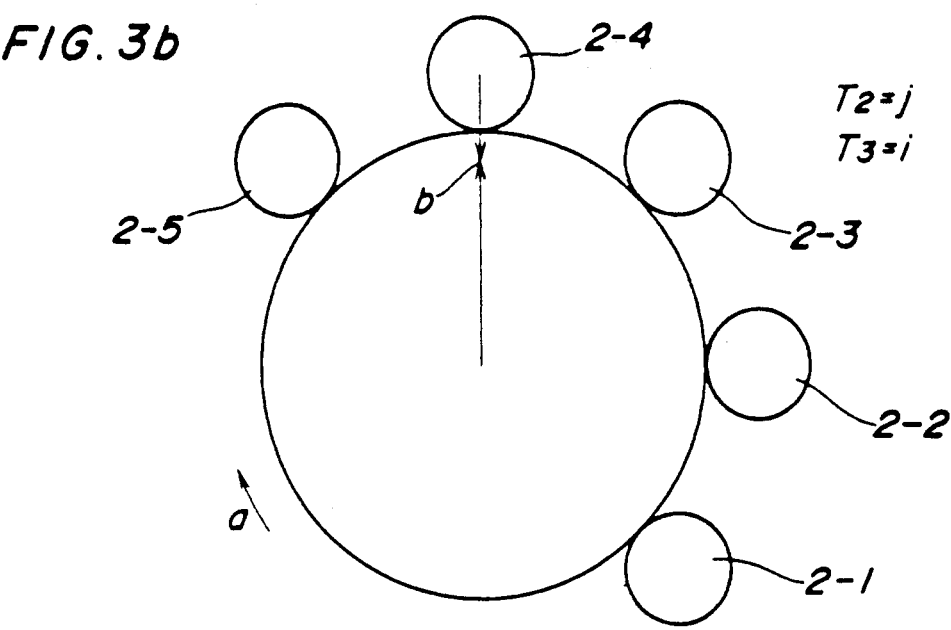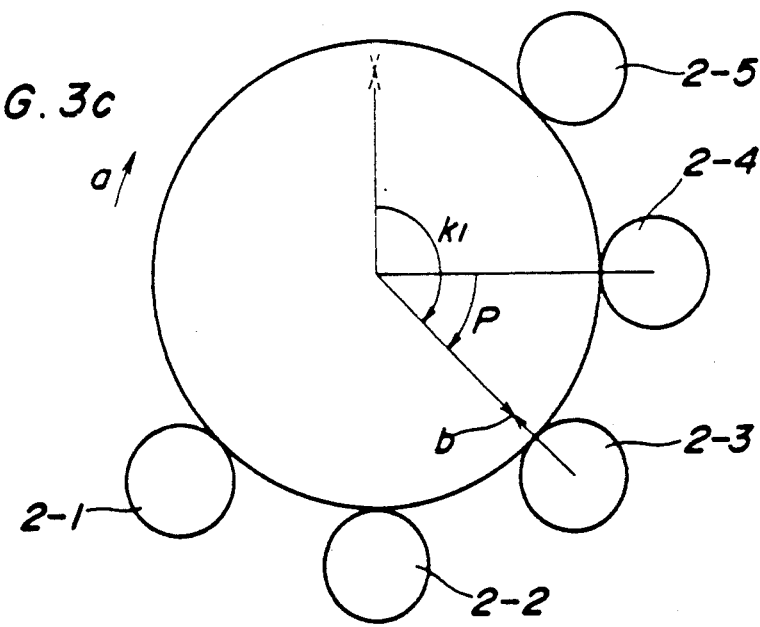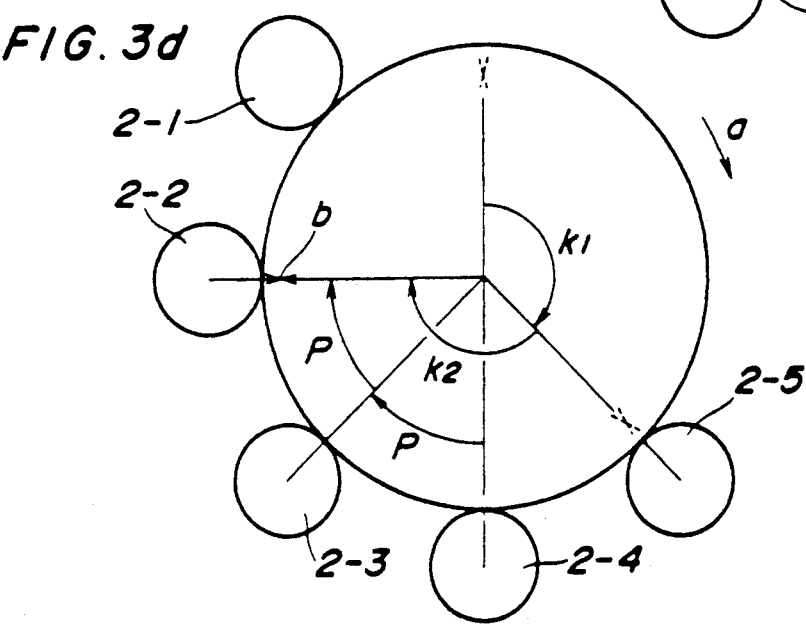

METHOD AND APPARATUS FOR DETECTING CRACKS IN BEARINGS

BACKGROUND OF THE INVENTION

This invention relates to a method and apparatus for detecting cracks in bearings, and more particularly to a method and apparatus for detecting microcracks in a bearing having rolling elements, during operation.

In general, if strain energy has been accumulated within a component part of a bearing, a phenomenon, such as plastic deformation, transformation, or breakage, may occur within the component part, when load is applied thereon, to release the strain engergy. At the same time, a microcrack may be developed at a portion of the component part where the phenomenon occurs. If this phenomenon continues to occur, the microcrack grows and finally brings about breakdown of the component part.

In the meanwhile, so-called acoustic emission has also long been known which is a phenomenon that the shock of release of the strain energy is propagated through the component part as an elastic wave.

Conventionally, devices for foreknowing the breakdown of bearings have been proposed, e.g. by Japanese Provisional Patent Publications (Kokai) Nos. 53-43588 and 63-271132, Japanese Provisional Utility Model Publication (Kokai) No. 60-172056, and U.S. Pat. No. 4,768,380. In such a device, a sensor detects acoustic emission (hereinafter referred to as "AE") due to occurrence of a microcrack in a component part of a slide bearing or a rolling bearing. The output, i.e. AE signal pulses, from the sensor is filtered by a filter to remove therefrom noise resulting from mechanical vibrations etc. The amplitude of the noise-removed AE signal pulses is compared with a predetermined reference value voltage), or AE signal pulses are counted by a counter and the frequency, i.e. the number of counted AE signal pulses per unit time is compared with a predetermined reference value, to thereby foreknow the breakdown of the bearing.

However, in the conventional device, since noise having the same frequency band as the AE signal cannot be removed even by the filter, the predetermined reference voltage value for determination of the amplitude of the AE signal must be set to a value considerably higher than the noise level in order to avoid erroneous determination of the AE signal. Therefore, the device cannot detect a microcrack unless a considerably great AE is produced, which makes early detection of the microcrack impossible.

Further, in the case of counting the AE signal pulses, there is a problem that the counted value is affected by noise in the AE signal, which makes accurate detection of the microcrack impossible.

SUMMARY OF THE INVENTION

It is therefore the object of the invention to provide a method and apparatus for detecting cracks in bearings, which are capable of detecting, during operation, microcracks developed in a bearing having rolling elements early and accurately by expecting the occurrence of acoustic emission (AE) caused by the microcracks.

To attain the above object, according to a first aspect of the invention, there is provided an apparatus for detecting a crack in a bearing including a stationary element, a moving element, and a plurality of rolling elements disposed between the stationary element and the moving element at equal intervals in a direction of movement of the moving element and movable in the direction.

The apparatus is characterized by comprising:
crack detecting means for detecting a signal characteristic of a crack in the bearing;
a rolling element position sensor for detecting a position of the rolling elements;
a moving element position sensor for detecting a position of the moving element; and
control means connected to the crack detecting means, the rolling element position sensor, and the moving element position sensor;
the control means determining, when an output signal from the crack detecting means is supplied thereto for the first time, based on at least one of position signals respectively supplied from the rolling element position sensor and the moving element position sensor, a condition of the at least one of position signals to be satisfied when the output signal from the crack detecting means is supplied to the control means the next time, monitoring the at least one of position signals thereafter, accumulating the output signal from the crack detecting means if the output signal is supplied to the control means when the at least one of position signals satisfying the condition is supplied to the control means, and determining whether or not the crack exists in the bearing based on a result of the accumulation.

Preferably, the result of the accumulation is a numerical value indicative of a number of times the output signal has been supplied to the control means accumulated by adding a predetermined numerical value to an immediately preceding numerical value accumulated, when the output signal from the crack detecting means is supplied to the control means.

Alternatively, the result of the accumulation is a value accumulated by adding a value corresponding to amplitude of the output signal from the crack detecting means to an immediately preceding value.

Preferably, the control means detects values of amplitude of the output signal from the crack detecting means for a predetermined time period, repeatedly effects the detection, determines distributions of the values of amplitude detected, and determines, based on the distributions, whether or not the crack exists in the bearing.

Alternatively, the control means detects duration times of the output signal from the crack detecting means for a predetermined time period, repeatedly effects the detection, determines distributions of the duration times detected, and determines, based on the distributions, whether or not the crack exists in the bearing.

According to a second aspect of the invention, there is provided a method for detecting a crack in a bearing including a stationary element, a moving element, a plurality of rolling elements disposed between the stationary element and the moving element at equal intervals in a direction of movement of the moving element and movable in the direction, and crack detecting means for detecting a signal characteristic of a crack in the bearing.

The method is characterized by comprising the steps of:

(1) detecting a position of the rolling elements;
(2) detecting a position of the moving element;

(3) determining, when an output signal from the crack detecting means is supplied for the first time, based on at least one of position signals respectively indicative of the position of the rolling elements and the position of the moving element detected in the steps (1) and (2), a condition of the at least one of position signals to be satisfied when the output signal from the crack detecting means is supplied the next time;

(4) monitoring the at least one of position signals thereafter;

(5) accumulating the output signal from the crack detecting means if the output signal is supplied when the at least one of position signals satisfying the condition is supplied; and (6) determining whether or not the crack exists in the bearing based on a result of the accumulation.

The above and other objects, features, and advantages of the invention will be more apparent from the ensuing detailed description taken in conjuntion with the accompanying drawings.

BRIEF DESCRIPTION OF THE DRAWINGS

FIGS. 3a to 3d are schematic diagrams useful in explaining defferent positions of component parts of an inner ring i, a rolling element 2, an outer ring 3, sensors 5, 6, 7, and a protrusion 101 of one embodiment according to the invention;

DETAILED DESCRIPTION

An embodiment of the invention will be described in detail below with reference to the drawings.

Figure 1:
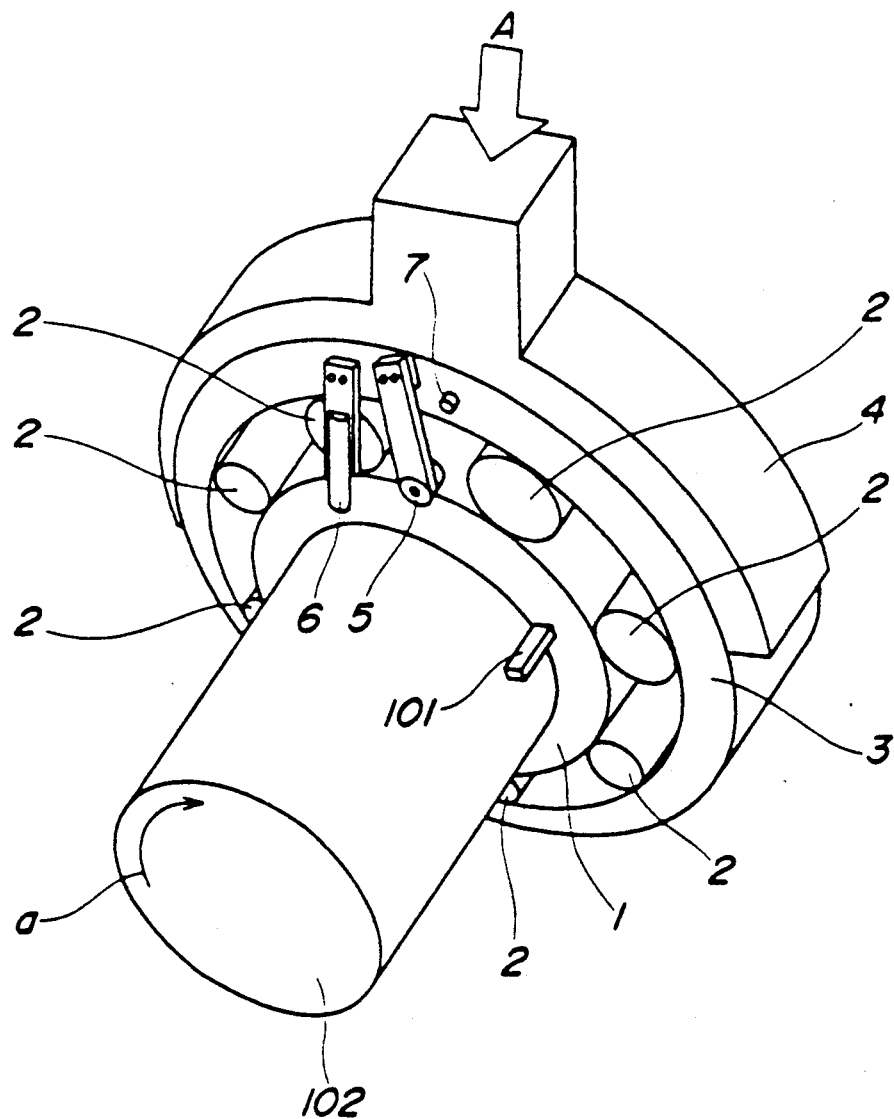
FIG. 1 is a perspective view of the whole arrangement of a radial bearing to which the invention is applied.

FIG. 1 shows a radial bearing to which the invention is applied. In the figure, reference numeral 1 designates an inner ring which is fitted on a rotary shaft 102 for rotation in unison therewith in the direction indicated by the arrow a at a speed of e.g. 3000 revolutions per minute. The rotary shaft 102 and the inner ring 1 are supported by a stationary outer ring 3, via a plurality of rolling elements 2 in the form of identical rollers disposed around the inner ring 1. Balls may be used in place of the rollers. Secured to the outer ring 3 is a loadapplying frame 4 for applying load on the outer ring 3 in the direction indicated by the arrow A. The rolling elements 2 are retained in circumferentially spaced relation at equal intervals by a cage, not shown, for movement or revolution around the inner ring 1 in the direction of the arrow a at a speed lower than the rotational speed of the inner ring 1 as the latter rotates.

The bearing shown in FIG. 1 is provided with a rolling element position sensor 5, an inner ring position sensor 6, an AE sensor 7, and a protrusion 101, all of which are component parts of the crack detecting apparatus according to the invention. The rolling element position sensor 5 comprises a photosensor fixed to the outer ring 3 such that its sensing head faces the orbital path of the rolling elements. The rolling element position sensor 5 generates a signal pulse whenever each of the rolling elements 2 passes the sensing head. The sensor 5 is not limited to the photosensor, but may be formed of a strain gauge, an eddy-current sensor, a vibrometer, an AE sensor, or the like.

The protrusion 101 is formed on the outer peripheral surface of the rotary shaft 102 at such a location that it is in contact with an end face of the inner ring 1. The inner ring position sensor 6 comprises a photosensor fixed to the the outer ring 3 such that its sensing head faces the orbital path of the protrusion 101. The inner ring position sensor 6 generates a signal pulse whenever the protrusion 101 passes the sensing head. The sensor 6 may be a contactless type.

The AE sensor 7 is secured to the outer ring 3 for detecting an elastic wave due to AE transmitted through the outer ring 3. Strain energy accumulated in the contact surface of the inner ring 1 or the outer ring 3 where it is brought into contact With the rolling element 2 is released through plastic deformation, transformation (e.g. from austenite to martensite), or breakage, when load is applied on the contact surface by the rolling element 2 passing the contact surface. As a result, a microcrack can occur and grow in the contact surface of the inner ring 1 or the outer ring 3. The shock of the release of the strain energy is propagated in the form of an elastic wave (AE). The elastic wave reaches the AE sensor 7 by way of the rolling elements 2 when the microcrack occurs in the inner ring 1 or directly when it occurs in the outer ring 3. As the crack grows, or as the pressure applied to the crack increases, the intensity of the elastic wave increases.

Figure 2:
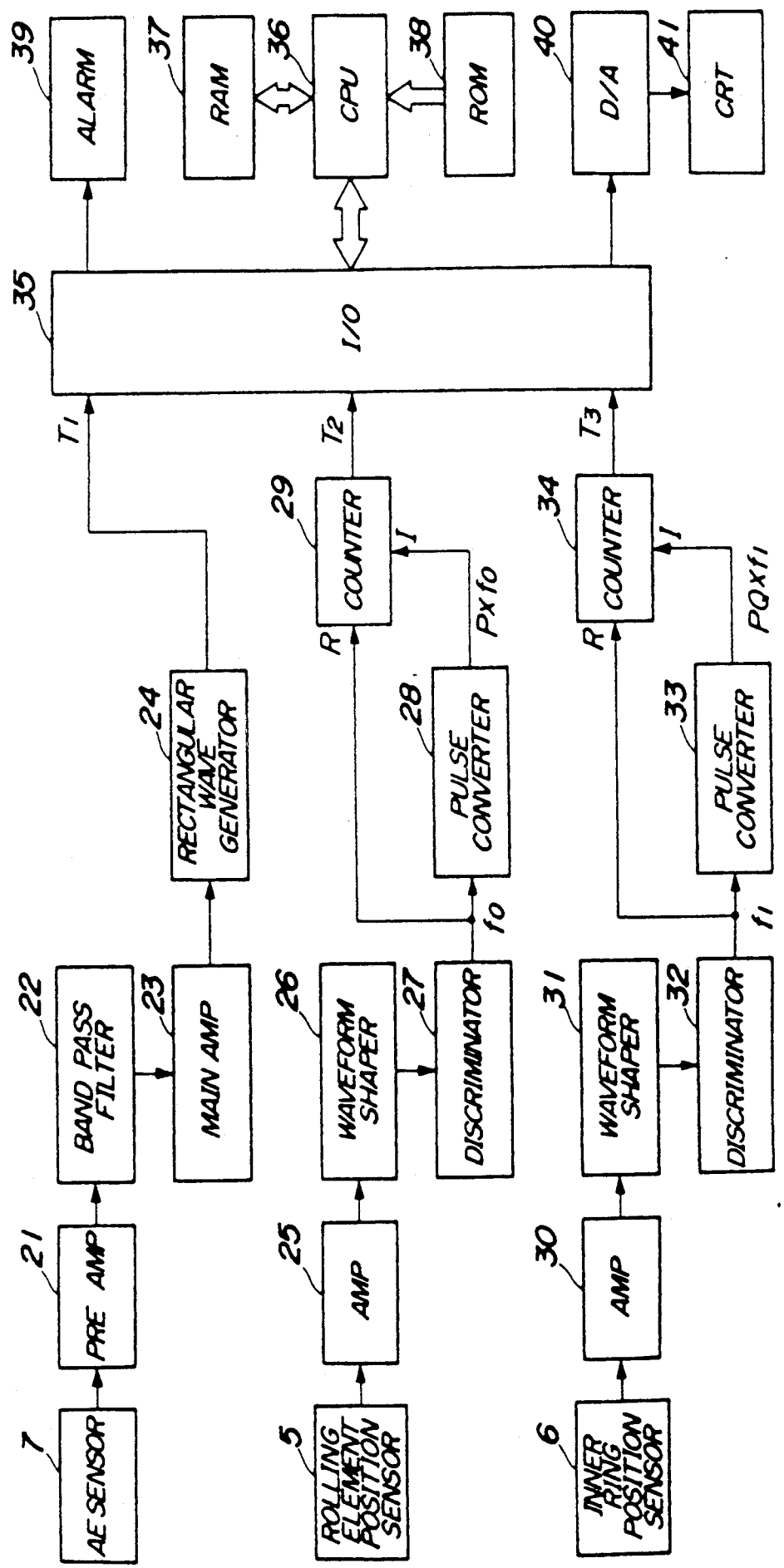
FIG. 2 is a diagram showing an electrical circuit of an apparatus for detecting cracks in a bearing according to the invention.
Figure 4A:
FIGS. 4a to 4e are waveform diagrams showing changes which an AE signal pulse undergoes until the AE signal pulse from the AE sensor 7 appearing in FIG. 2 passes a rectangular wave-generating device 24.
Figure 4B:
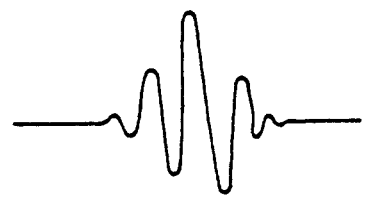
Figure 4C:
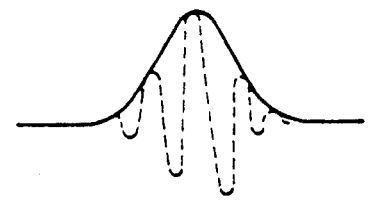

FIG. 2 shows an electric circuit which forms the apparatus according to the invention. In the figure, the AE sensor 7 is connected to a rectangular wave generator 24 via a pre-amplifier 21, a band pass filter 22 for passing frequencies of a band of 100 to 500 kHz, and a main amplifier 23. The output side of the rectangular wave generator 24 is connected to an input-output circuit 35 of a microcomputer for supplying the output $T_1$ of the rectangular wave generator 24 to the input-output circuit 35. More specifically, as shown in FIG. 4, the output (FIG. 4a) of the AE sensor 7 is amplified by the pre-amplifier 21 and the main amplifier 23 while low and high frequency components are removed by the band pass filter 22 (FIG. 4b). Then the rectangular wave generator 24 carries out envelope detection of the AE signal pulse (FIG. 4c). Only when the level of the resulting detected signal pulse (indicated by the solid line in FIG. 4c) exceeds a predetermined threshold value (indicated by the broken line in FIG. 4d), the generator 24 generates a rectangular wave signal $T_1$ (FIG. 4e) having a pulse width corresponding to the duration time over which the level of the signal pulse exceeds the threshold value.

The rolling element position sensor 5 is connected to a discriminator 27 via an amplifier 25 and a waveform shaper 26. More specifically output pulses from the rolling element position sensor 5 are amplified by the amplifier 25 and shaped by the waveform shaper 26, and the discriminator 27 generates pulses having the same frequency as the pulses supplied from the waveform shaper 26 and a predetermined waveform. An output pulse is generated from the discriminator 27 whenever each rolling element 2 passes a monitoring point, i.e. the sensing head of the sensor 5. Therefore, the frequency $f_0$ (Hz) of the output pulses corresponds to the number of rolling elements passing the monitoring point Within one second.

The output side of the discriminator 27 is connected to a pulse converter 28 as well as to a reset terminal R of a counter 29. The output side of the pulse converter 28 is connected to an input terminal I of the counter 29. The output side of the counter 29 is connected to the input-output circuit 35 of the microcomputer. In the pulse converter 28 a pulse signal having a frequency $f_0$ from the discriminator 27 is converted into a pulse signal having a frequency $P \times f_0$, which is the product of the frequency $f_0$ multiplied by an integer P. Thus the resulting converted pulse signal has a pulse repetition period which is 1/P times as long as the time interval from a time point one of the rolling elements 2 passes the monitoring point to a time point the next rolling element 2 passes the monitoring point. The counter 29 counts the pulses having the frequency of $P \times f_0$ supplied via its input terminal I from the pulse converter 28, and the counted value $T_2$ is supplied to the input-output circuit 35. Further the counter 29 is reset whenever a pulse of the signal having the frequency of $f_0$ is supplied thereto via its reset terminal R from the discriminator 27 in other words, the counter 29 counts from 0 to P−1 during the time period over which two adjacent rolling elements 2 pass the monitoring point for the rolling element position sensor 5. Assuming that the total number of the rolling elements 2 spaced at equal intervals is Q, the unit counted value 1 corresponds to a rotational angle 360/PQ degrees of a rolling element 2.

Further, the value of P is determined in dependence on the width of a waveform (indicated by the solid line in FIG. 4c) of the AE signal after envelope detection. More specifically, if the width is narrower, P is set to a larger value to improve the accuracy of crack detection.

The inner ring position sensor 6 is connected, similarly to the rolling element position sensor 5 to a discriminator 32 via an amplifier 30 and a waveform shaper 31. The discriminator 32 generates a pulse signal having a frequency $f_1$ (Hz) whenever the protrusion 101, which rotates in unison with the rotation of the inner ring 1, passes a monitoring point or the sensing head of the inner ring position sensor 6. The frequency $f_1$ (Hz) corresponds to the number of times the protrusion 101 passes the monitoring point for the sensor 6 within one second.

The output side of the discriminator 32 is connected to a pulse converter 33 as well as to a reset terminal R of a counter 34. The output side of the pulse converter 33 is connected to an input terminal I of the counter 34. The output side of the counter 34 is connected to the input-output circuit of the microcomputer. In the pulse converter 33 a pulse signal having a frequency $f_1$ from the discriminator 32 is converted into a pulse signal having a frequency PQ x f1, which is the product of the frequency $f_1$ multiplied by an integer PQ. Thus the resulting pulse signal has a pulse repetition period which is 1/PQ times as long as the time interval from a time point the protrusion 101 passes the monitoring point to a time point the protrusion 101 passes the monitoring point the next time. The counter 34 counts the signal pulses having the frequency of PQ x $f_1$ which is supplied thereto via its input terminal I from the pulse converter 33, and the counted value $T_3$ is supplied to the input-output circuit 35. Further the counter 34 is reset whenever a pulse of the pulse signal having the frequency $f_1$ is supplied thereto via its reset terminal R from the discriminator 32. In other words, the counter 34 counts from 0 to pQ−1 during the time period from the time point the protrusion 101 passes the monitoring point to the time point the protrusion 101 passes the monitoring point the next time. The unit counted value 1 of the counter 34 corresponds to a rotational angle of 360/PQ degrees of the protrusion 101.

As described above, the unit counted value of the counter 29 also corresponds to the rotational angle of 360/PQ degrees. Therefore, the unit counted values of the counters 29 and 34 correspond to the same rotational angle of the rolling element 2 and the protrusion 101 (i.e. the inner ring 1).

Based on this correspondence between the unit counted value 1 of both the counters 29 and 34 and the rotational angle of 360/PQ degrees, the following description of the invention will be made in a simplified manner. That is, 360/PQ degrees, which corresponds to the unit counted value 1, is regarded as a unit rotational angle and hence the rotational angles of the rolling element 2 and the protrusion 101 (the inner ring 1) are expressed by multiples (which correspond to the counted values of the counters 29, 34) of the unit rotational angle. For example, an angle formed by adjacent ones of the rolling elements 2 can be expressed as the integer of P, and an angle (360 degrees) corresponding to one rotation of the protrusion 101 or one of the rolling elements 2 can be expressed as the integer of PQ. In the following description, the rotational angle is expressed based on the unit rotational angle which corresponds to 360/PQ degrees.

An alarm 39 is connected to the input-output circuit 35 of the microcomputer, and a CRT display 41 is also connected to the circuit 35 via a digital/analog converter 40. Also connected to the input-output circuit 35 via a bus is a CPU 36 to which are connected a RAM 37 and a ROM 38 via the bus Next, the method of detecting cracks in a bearing according to the invention will be described in detail with reference to FIGS. 3a to 3d in which are shown the inner ring 1, the rolling elements 2 the outer ring 3, the sensors 5, 6, 7, and the protrusion 101 in different positions.

Figure 3A:
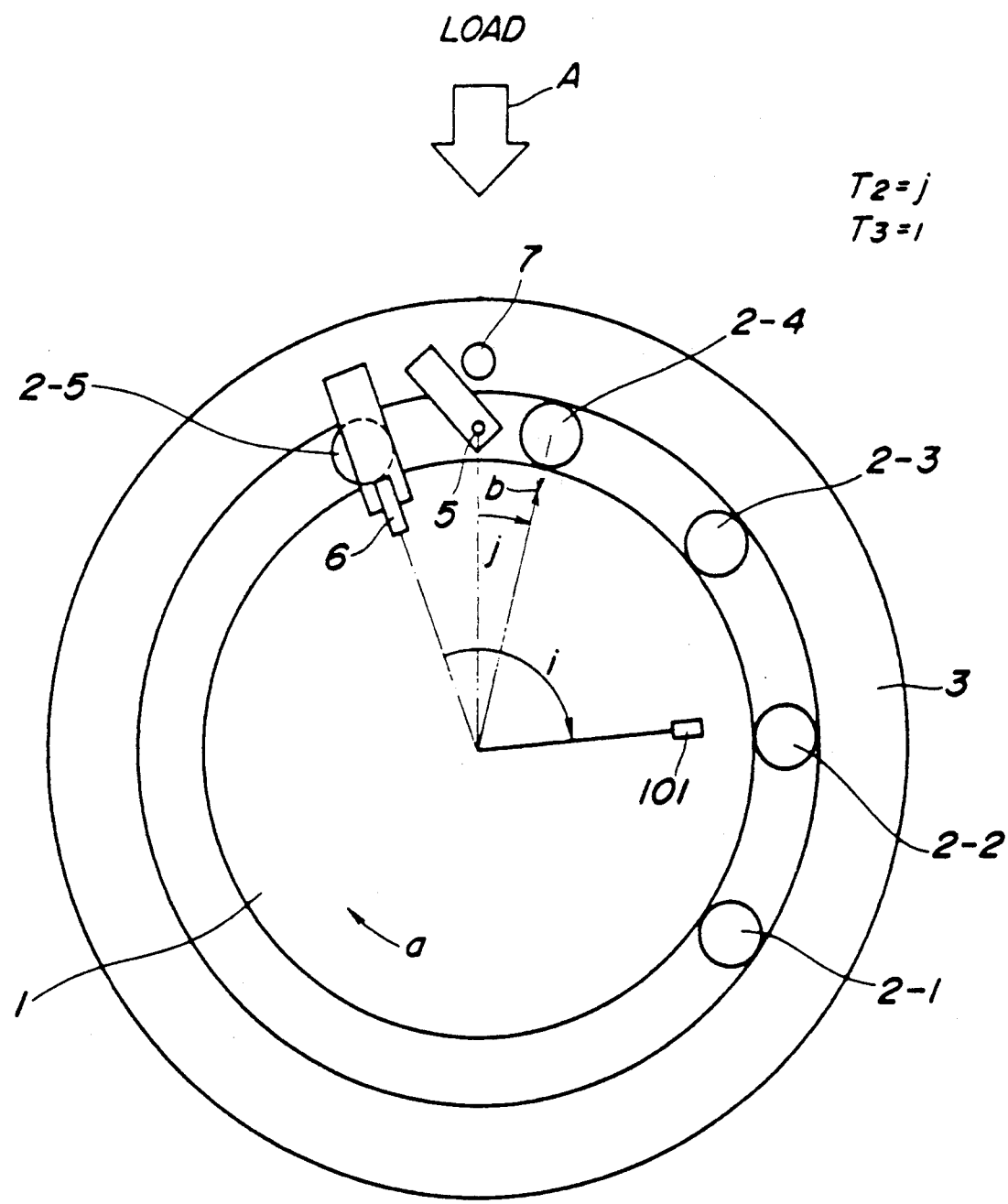

A microcrack usually occurs in the inner ring 1 or in the outer ring 3. First, let it be assumed that a microcrack has occurred in the inner ring 1, i.e. at a location indicated by X (the solid line) in FIGS. 3a and 3b. With reference to FIG. 3a, and FIG. 3b which shows in a simplified manner the angular position of the rolling elements and the inner ring shown in FIG. 3a, suppose that when the protrusion 101 on the inner ring 1 has rotated in the direction of the arrow a by a rotational angle of i (corresponding to a counted value $T_3 = i$ of the counter 34) after passing the inner ring position sensor 6, one 2-4 of the rolling elements is located above the microcrack b (indicated by the solid line X), so that AE has occurred and the rectangular wave signal $T_1$ has been generated. Also suppose that, at this time point, the rolling element 2-4 has rotated in the direction a by a rotational angle of j (corresponding to a counted value $T_2 = j$ ($0 \leq j \leq P-1$) of the counter 29) after passing the rolling element position sensor 5.

The CPU 36 calculates a value $T_4$ ($=T_3-T_2$) by subtracting the counted value $T_2$ of the counter 29 from the counted value $T_3$ of the counter 34 when the rectangular wave signal $T_1$ is supplied thereto. The calculated value $T_4$ is equal to (i - j).

Then suppose that, as shown in FIG. 3c, the inner ring 1 has further rotated in the direction of the arrow a by an angle of $K_1$ from the position shown in FIG. 3b so that the microcrack b in the inner ring 1 has come under the rolling element 2-3 adjacent to the rolling element 2-4, and accordingly AE has occurred and the rectangular wave signal $T_1$ has been generated.

At this time point, since the angle formed between the rolling element 2-4 and the rolling element 2-3 is P and the counted value $T_2$ is a value obtained with respect to the rotation of the rolling element 2-4, the counted value $T_2$ is expressed as follows:

$$T_2 = j + (k_1 - P) - S_1 P \ (0 \leq T_2 \leq P-1)$$

where $S_1$ is an integer for satisfying the condition of $0 \leq T_2 \leq P-1$, which is based on the fact that the counter 29 is reset, as described above, whenever the counted value $T_2$ reaches P.

The counted value $T_3$ of the counter 34 is expressed as follows:

$$T_3 = i + K_1 - r_1 PQ \ (0 \leq T_3 \leq PQ-1)$$

where $r_1$ is an integer for satisfying the condition of $0 \leq T_3 \leq PQ-1$, which is based on the fact that the counter 34 is reset, as described above whenever the counted value $T_3$ reaches PQ.

Therefore, $T_4 (=T_3-T_2)$, which is calculated when the rectangular wave signal $T_1$ is supplied to the CPU 36, is obtained as follows:

$$T_4 = i - j + P(1 + S_1 - r_1 Q)$$

Then, suppose that, as shown in FIG. 3d, the inner ring 1 has further rotated by an angle of $K_2$ from the position shown in FIG. 3c and the microcrack b has come under the rolling element 2-2 adjacent to the rolling element 2-3, so that AE has occurred and the rectangular wave signal $T_1$ has been generated.

At this time point, $T_2$ and $T_3$ are obtained as follows:

$$T_2 = j + (k_1 - P) + (K_2 - P) - S_2 P \ (0 \leq T_2 \leq P-1)$$

$$T_3 = i + K_1 + K_2 - r_2 PQ \ (0 \leq T_3 \leq PQ-1)$$

where $S_2$ and $r_2$ are integers for satisfying the respective conditions of $0 \leq T_2 \leq P-1$ and $0 \leq T_3 \leq PQ-1$, which are based on the fact that the counters 29, 34 are reset as mentioned above. Therefore, $T_4 (=T_3-T_2)$, which is calculated when the rectangular wave signal $T_1$ is supplied to the CPU 36, is expressed as follows:

$$T_4 = i - j + P(2 + S_2 - r_2 Q)$$

Suppose that in general, the inner ring 1 has rotated by an angle of $k_l$ in the arrow direction from a position where AE occurred so that the microcrack b has come under one of the rolling elements, whereby AE has occurred and the rectangular wave signal $T_1$ has been generated. l is the ordinal number indicating the order of occurrence of the AE (l = 1, 2, 3, ... n).

In this case, $T_2$ and $T_3$ at the time of nth occurrence of AE can be generally expressed as follows:

$$T_2 = j + \sum_{l=1}^{n} k_l - nP - S_n P \ (0 \leq T_2 \leq P-1)$$

$$T_3 = i + \sum_{l=1}^{n} k_l - r_n PQ \ (0 \leq T_3 \leq PQ-1)$$

where $S_n$ and $r_n$ are integers for satisfying the respective conditions of $0 \leq T_2 \leq P-1$ and $0 \leq T_3 \leq PQ-1$, which are respectively based on the facts that the counter 29 is reset whenever the counted value $T_2$ reaches P and that the counter 34 is reset whenever the counted value $T_3$ reaches PQ.

Therefore, $T_4 (=T_3-T_2)$, which is calculated by the CPU 36 when the rectangular wave signal $T_1$ resulting from the nth occurrence of AE is supplied thereto, is obtained as follows:

$$T_4 = i - j + P(n + S_n - r_n Q)$$

According to this equation, since n, $S_n$, $r_n$, and Q are all integers, $P(n + S_n - r_n Q)$ is a multiple of P. Therefore, it is clear from this equation that AE occurs when $T_4$ ($=T_3-T_2$) becomes equal to a value obtained by adding a multiple of P to the difference (i−j) between the counted value $T_2$ (=j) of the counter 29 and the counted value $T_3$ (=i) of the counter 34 after the initial rectangular wave signal $T_1$ was generated (zeroth occurrence of AE).

Therefore, $T_4$ is calculated after a time point AE occurred for the first time so that the rectangular wave signal $T_1$ was generated for the first time, and it is possible from the calculated $T_4$ to presume that the rectangular wave signal $T_1$ is generated at a time point $T_4$ becomes equal to a value obtained by adding the product of P multiplied by an integer (including zero to (i−j) which is a value of $T_4$ when AE occurred for the first time.

More specifically, the CPU 36 calculates $T_4$ ($=T_3-T_2$) based on the counted values $T_2$ and $T_3$ from the respective counters 29 and 34 when the rectangular wave signal $T_1$ is supplied thereto for the first time and the result $T_{40}$ ($=i-j$) of the calculation is stored into the RAM 37. $T_4$ is calculated based on the counted values $T_2$ and $T_3$ supplied thereafter and the difference $T_4-T_{40}$ between the calculation result $T_4$ and the aforementioned $T_{40}$ is calculated. If the rectangular wave signal $T_1$ is supplied when the difference $T_4-T_{40}$ is equal to the product of P multiplied by an integer (including zero), 1 is added to the immediately preceding value (the initial value is 0) stored at an address of the RAM 37 (the RAM 37 has addresses to which respective address numbers of I to PQ are allotted). If the AE sensor 7 detects noise to thereby generate the rectangular wave signal $T_1$, 1 is not added to the value stored at the same address of the RAM, but if the supply of the rectangular wave signal $T_1$ has been generated due to occurrence of the microcrack, 1 is added to the value stored at the same address of the RAM 37.

Figure 5:
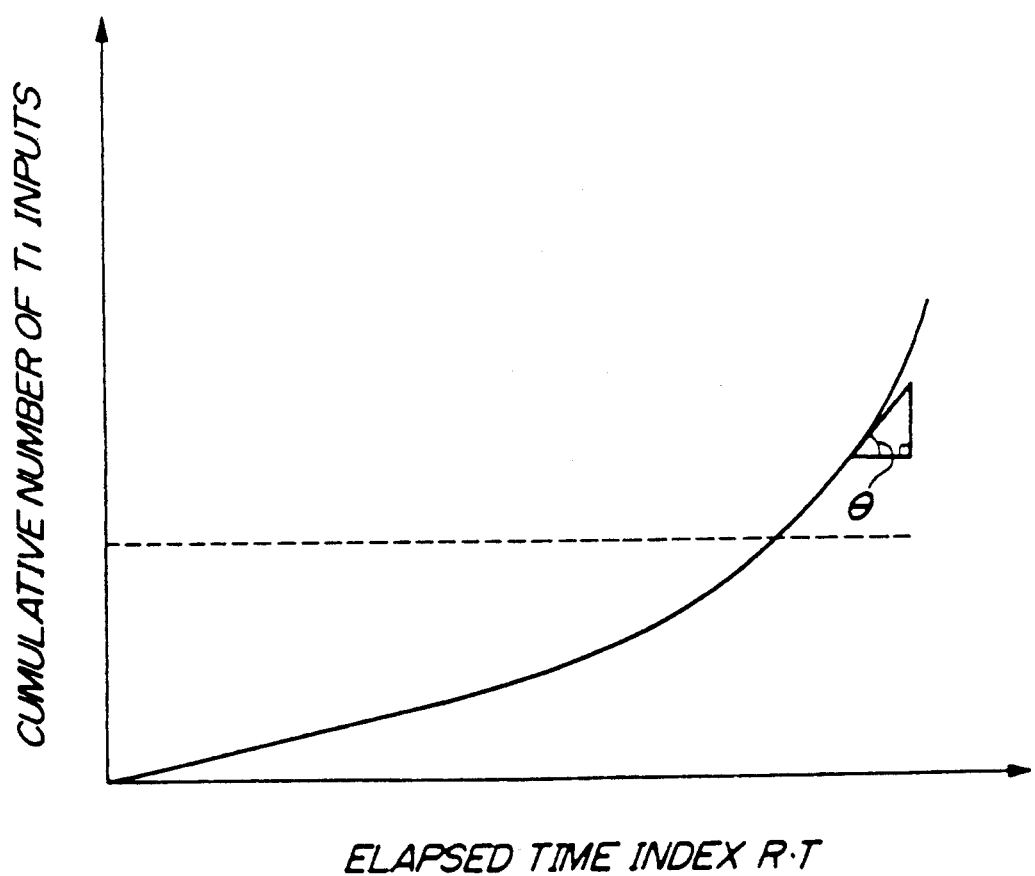
FIG. 5 is a graph showing the change in the cumulative number of $T_1$ inputs relative to time elapsed.

The added value, i.e. the cumulative number of inputs of the rectangular wave signal $T_1$ to the inputoutput circuit 35 varies with the lapse of time as shown in FIG. 5. In the graph of FIG. 5, the ordinate represents the cumulative number of inputs of the rectangular wave signal $T_1$, and the abscissa represents the elapsed time index (R.T) which is plotted as if AE occurs at equal time intervals. In the present embodiment in which the outer ring is stationary and the inner ring is rotated, and at the same time a microcrack occurs in the inner ring the elapsed time index R.T is expressed as follows:

$$R \cdot T = X \cdot Q - Y$$

where X represents the number of times the protrusion 101 has passed the inner ring position sensor 6 after generation of the first $T_1$ signal pulse, Y the number of times rolling elements 2 have passed the rolling element position sensor 5 after generation of the first $T_1$ signal pulse, and Q the total number of the rolling elements.

In the case where a microcrack occurs in the outer ring, R.T can be expressed as $R \cdot T = Y$.

According to FIG. 5, as the microcrack grows, AE occurs with greater intensity, and hence the rectangular wave signal $T_1$ is supplied to the inputoutput signal 35 at an increased frequency which results in rapid increase of the cumulative number of $T_1$ inputs. The CPU 36 supplies an alarm command to the alarm 39 when the cumulative number of $T_1$ inputs has exceeded a predetermined value indicated by the broken line in the figure. Preferably, a plurality of such predetermined values are provided for comparison with the cumulative number of $T_1$ inputs, which correspond respectively to different stages of growth of the microcrack including initial state of a germinal microcrack and a final stage of growth causing breakdown of the bearing to thereby enable to monitor the growth of microcrack and display the actual stage on the CRT display 41. This makes it possible to use a bearing, in which a microcrack has occurred and is growing, to the maximum possible extent, and take a suitable counter measure, e.g. replacement of the bearing, before the microcrack reaches the final stage.

Further, in addition to the monitoring as to whether the cumulative number of $T_1$ inputs exceeds the predetermined value, the increase rate $\tan\theta$ of the cumulative number of $T_1$ inputs may be monitored and the alarm may be given when the increase rate $\tan\theta$ has exceeded a predetermined value, to thereby prevent the bearing from breaking down due to rapid growth of the microcrack.

The cumulative number of $T_1$ inputs stored in the RAM 37 is cleared whenever a predetermined time period has elapsed after the rectangular wave signal $T_1$ was supplied to the input-output circuit 35 for the first time or whenever the inner ring 1 has rotated a predetermined number of times, whereby the cumulative number of $T_1$ inputs due to noise is cleared.

The above described embodiment is directed to the case where a microcrack b occurs in the inner ring 1. However, in the case where a microcrack occurs in the outer ring 3, AE may occur to generate the rectangular wave signal $T_1$ whenever the counted value $T_2$ of the counter 29 assumes a certain value irrespective of the counted value $T_3$ of the counter 34. Therefore, in order to detect a microcrack occurring in the outer ring 3, the CPU 36 operates such that the counted value $T_2$ supplied from the counter 29 is stored into the RAM 37 when the first rectangular wave signal $T_1$ is supplied to the CPU 36. The CPU 36 monitors the counted value $T_2$ supplied thereto thereafter, and adds 1 to a value stored at an address of the RAM 37 having the address number identical to the stored counted value $T_2$, if the rectangular wave signal $T_1$ is supplied to the CPU 36 when the counted value $T_2$ becomes equal to the stored value. The cumulative number obtained by this addition is compared with a predetermined value or the increase rate of the cumulative number is compared with a predetermined value to thereby determine the occurrence of a microcrack in the outer ring similarly to the case where the microcrack occurs in the inner ring 1. Therefore, in this case, the circuit elements indicated by reference numerals 6, and 30 to 34 in FIG. 2 can be omitted.

In the above described embodiment, the inner ring 1 rotates while the outer ring 3 is stationary However, the present invention may also be applied to a bearing where the inner ring is stationary while the outer ring rotates. More specifically, in such a bearing, a protrusion 101 is provided on the outer ring, and a inner ring position sensor 6 is provided on the inner ring such that the sensor faces the orbital path of the protrusion, and at the same time a rolling element position sensor 5 is fixed to the inner ring.

Figure 6:
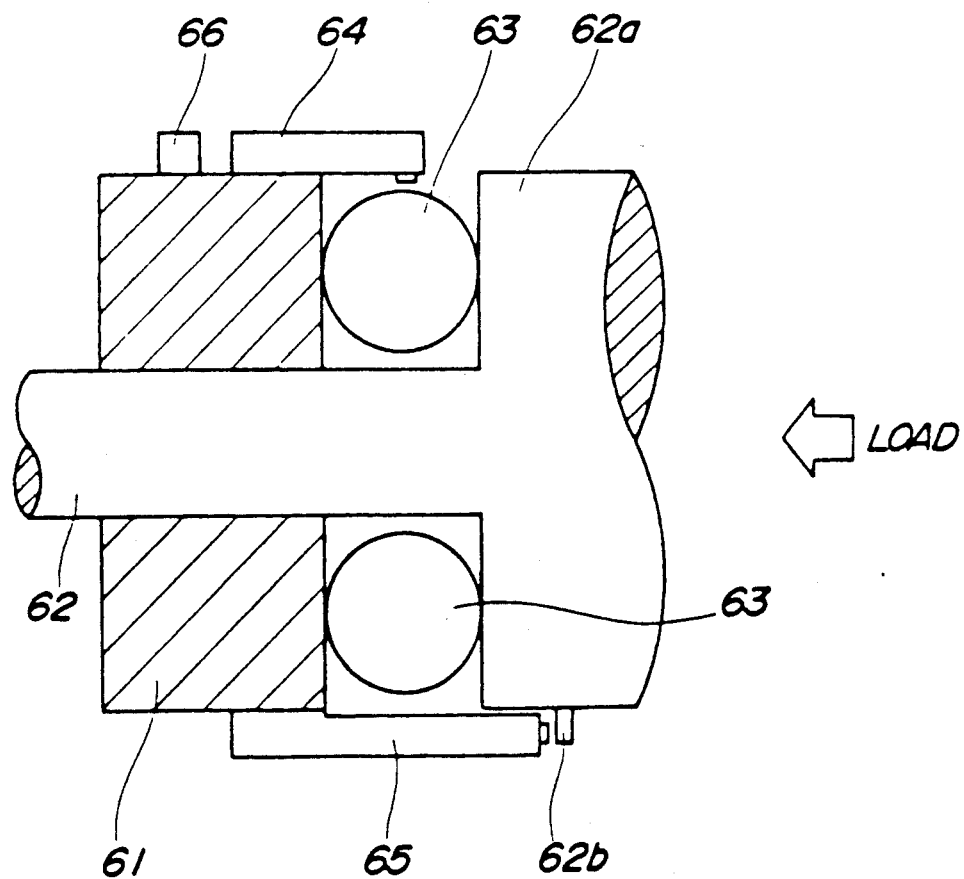
FIG. 6 is a transverse sectional view of a thrust bearing to which the invention is applied.

Further, although in the above described embodiment, the invention is applied to a radial bearing, it may also be applied to a thrust bearing as shown in FIG. 6. In the figure, the thrust bearing comprises a stator 61, a rotary shaft 62 rotatably fitted through the stator 61, a collar 62a radially extending from the rotary shaft 62, and a plurality of rolling elements 63 arranged around the rotary shaft between the stator 61 and the collar 62a, the rolling elements 63 being circumferentially spaced from each other at equal intervals.

A rolling element position sensor 64 is provided on the stator 61 such that it faces the orbital path of the rolling elements 63, a rotary shaft position sensor 65 is provided on the stator 61 such that it faces the orbital path of a protrusion 62b provided on the collar 62a of the rotary shaft 62m and an AE sensor 66 is provided on the stator 61. Thus, the invention can be applied to the thrust bearing quite similarly to the above case where it is applied to the radial bearing.

Further, the present invention may be applied to a slide bearing. A slide bearing in general comprises a stator, a moving element for linear movement, and a plurality of rolling elements interposed between the stator and the moving element at equal intervals which can roll in a direction parallel to the the linear movement of the moving element. In such a slide bearing, the invention can be applied by providing a plurality of protrusions on the moving element at equal intervals longer than those for the rolling elements, Q being defined as the number of rolling elements which can be received between adjacent ones of the protrusions.

Figure 7:
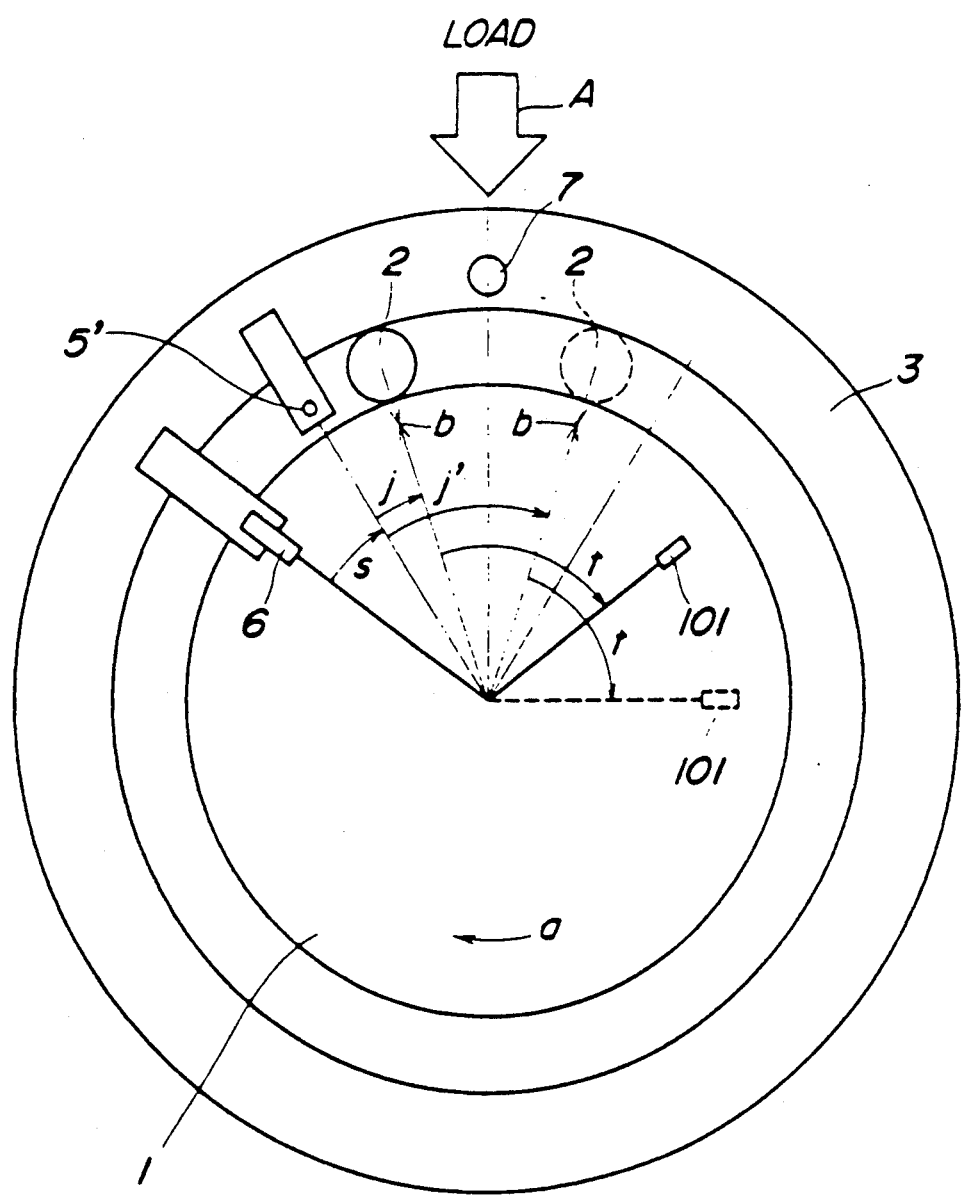
FIG. 7 is a schematic diagram showing a variation of the embodiment shown in FIG. 3.

In a thrust bearing and a slide bearing as described above, load is evenly applied on the rolling elements, so that when any of the rolling elements comes under or over microcracks, AE occurs with identical intensity provided that the microcracks are equal in size to each other. However, in a radial bearing as described before, load is not evenly applied on the rolling elements, so that if one of the rolling elements on which a light load is applied comes under or over a microcrack, AE does not occur with sufficient intensity, which makes it difficult to detect the microcrack properly. To eliminate this incovenience, a further embodiment of the invention is provided, which is improved over the aforedescribed embodiment applied to the radial bearing. The further embodiment is shown in FIG. 7. The following description is limited to features peculiar to the further embodiment. Description of elements and parts identical to those of the previous embodiment is omitted.

In FIG. 7, there is shown a sector defined by two two-dot chain lines, with its central line (indicated by one-dot chain line) extending in a direction in which load A is applied. This sector is defined as a loaded region. The sector has an angle of 360°/Q (Q is the number of rolling elements 2), which is equal to the rotational angle formed by adjacent ones of the rolling elements. In this loaded region, only one of the rolling elements can always necessarily exist. The load A is applied on the rolling element existing within the loaded region, whereas those existing outside the loaded region bear very little load.

A rolling element position sensor 5' is fixed to the outer ring 3 such that its sensing head faces the orbital path of the rolling elements at the inlet end of the loaded region.

An AE sensor 7 is arranged on the outer ring 3 at a location on the one-dot chain line indicating the center of the loaded region.

Suppose that when one of the rolling elements 2 has rotated through an angle of j (which corresponds to the counted value $T_2$ (=j) of the counter 29) after passing the rolling element position sensor 5', one of the rolling elements has come over a microcrack b (indicated by the solid line X) occurring in the inner ring 1 so that AE has occurred and the rectangular wave signal $T_1$ has been supplied to the input-output circuit 35. If the rotational angle formed between the inner ring position sensor 6 and the rolling element position sensor 5' is s (constant) and the rotational angle formed between the microcrack b and the protrusion 101 on the inner ring 1 is t (constant), the rotational angle formed between the inner ring position sensor 6 and the protrusion 101 is s+j+t (which corresponds to the counted value $T_3$ (=s+j+t) of the counter 34). Therefore at this time point, $T_4$ (=$T_3-T_2$)=s+t.

The inner ring 1 further rotates in the direction of the arrow a and AE occurs again when the microcrack returns to the loaded region and comes to a position below one of the rolling elements. The microcrack b, the rolling element 2 and the protrusion 101 at this time point are shown by the broken lines. If the rotational angle formed between the rolling element 2 and the rolling element position sensor 5' at this time point is j' (which corresponds to $T_2$ (=j')), since the relative position of the microcrack b and the protrusion 101 is constant, the rotational angle formed between the inner ring position sensor 6 and the protrusion 101 is s+j'+t (which corresponds to $T_3$ (=s+j'+t)). Therefore, at this time point, $T_4$=s+t.

As will be learned from the above, when AE occurs in the loaded region, $T_4$ always assumes the same value with respect to the same microcrack.

The CPU 36 calculates $T_4$ (=$T_3-T_2$) based on the counted values $T_2$ and $T_3$ when it is supplied with the rectangular wave signal $T_1$, and the resulting value $T_{40}$ is stored into the RAM 37. Thereafter, if $T_4$, which is calculated based on the $T_3$ and $T_2$ supplied, agrees with the stored value $T_{40}$ when $T_1$ is supplied to the CPU 36, 1 is added to the immediately preceding value (the initial value is 0) stored at an address of the RAM 37.

In this way it is possible to detect a microcrack in a radial bearing accurately and at an early stage of growth of the microcrack.

Further, in the above described embodiments, the cumulative number of $T_1$ inputs is obtained by cumulating 1 by the CPU 36 whenever the rectangular wave signal generated by the rectangular wave generator 24 shown in FIG. 2 is supplied to the inputoutput circuit 24. However, as an alternative method a cumulative value of $T_1$ inputs may be obtained by generating a rectangular wave signal $T_1$ having amplitude commensurate with the intensity of the AE (which is greater as the microcrack is larger) by the rectangular wave generator 24, and cumulating the amplitude value of each rectangular wave signal $T_1$. This method makes it possible to raise an alarm depending not only on the frequency of occurrence of AE but also on the intensity of AE.

Other embodiments of the method according to the invention will be described below with reference to FIGS. 8 and 9. The embodiments both comprise continuously monitoring signal pulses (one of which is indicated by the solid line in FIG. 4c) obtained by envelope detection of output signal pulses from the AE sensor 7, determining the amplitude distribution of the monitored signal pulses or the duration distribution of same during a predetermined short period of time, and detecting a microcrack based on the amplitude distribution or the duration distribution.

Figure 4D:
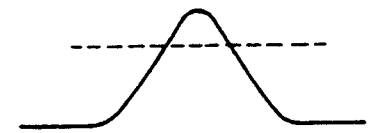
Figure 4E:

According to one of the embodiments, a predetermined threshold value indicated by the broken line in FIG. 4d is set, for example, at 70 dB Detection of signal pulses after envelope detection (one of which is indicated by the solid line in FIG. 4d) the amplitude of which exceeds 70 dB is effected for a predetermined very short period of time $\Delta$RT. The same detection is repeated to thereby detect amplitude distributions of the detected signal pulses. FIG. 8 shows an amplitude distribution of the signal pulses after envelope detection which are detected during the predetermined very short period of time $\Delta$RT. More specifically, the abscissa represents the amplitude in dB, and the ordinate represents in logarithm the number $\Delta N_T$ of signal pulses after envelope detection detected during the predetermined very short period of time and having amplitude shown by the ordinate.

Figure 8:
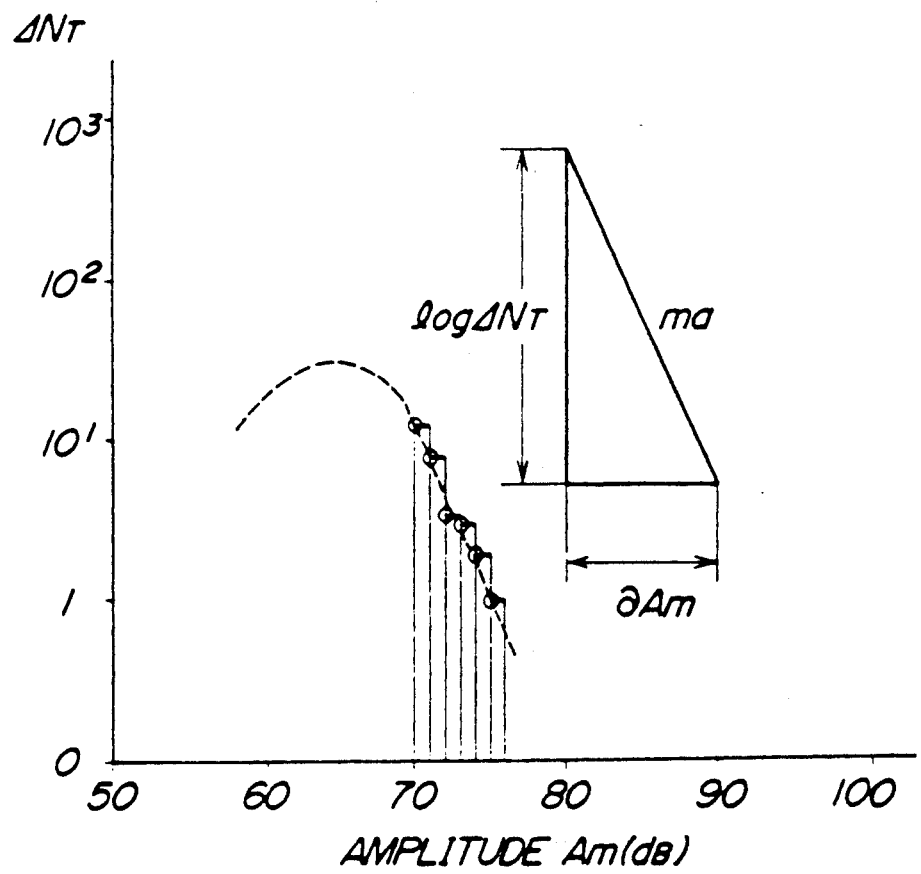
FIG. 8 is a diagram showing an amplitude distribution of signal pulses after envelope detection detected during a predetermined very short period of time $\Delta RT$.

In FIG. 8, if the slope of distribution of amplitude Am of the signal pulses after envelope detection detected during the very small period of time $\Delta$RT is designated by Ma, Ma is expressed as follows:

$$Ma = (\partial \log \Delta N_T)/\partial Am$$

In general, if the microcrack is very small, the amplitude of a signal pulse after envelope detection rarely exceeds the threshold value, and even if it exceeds the value it is relatively small However, as the microcrack grows, AE becomes intenser so that the amplitude of a signal pulse after envelope detection becomes larger and hence an increased number of signal pulses after envelope detection have relatively great amplitude. Therefore, the slope Ma of distribution of amplitude Am is monitored and when the slope Ma exceeds a predetermined value an alarm command signal is supplied from the CPU 36 to the alarm 39, whereby the microcrack is detected with high accuracy.

Further, according to the other of the embodiments, detection of signal pulses (indicated by the solid line in FIG. 4d) after envelope detection the amplitude of which exceed a predetermined threshold value (indicated by the broken line in FIG. 4d), is effected for the predetermined very small period of time ΔRT. The duration time (corresponding to the pulse width shown in FIG. 4e) during which the voltage of each signal pulse exceeds the threshold value is detected. FIG. 9 shows a distribution of the duration times D detected during the predetermined very small period ΔRT. More specifically, the abscissa represents the duration time D, and the ordinate represents in logarithm the number $\Delta N_T$ of the signal pulses which have duration times indicated by the abscissa and have occurred during the predetermined very small period of time ΔRT.

Figure 9:
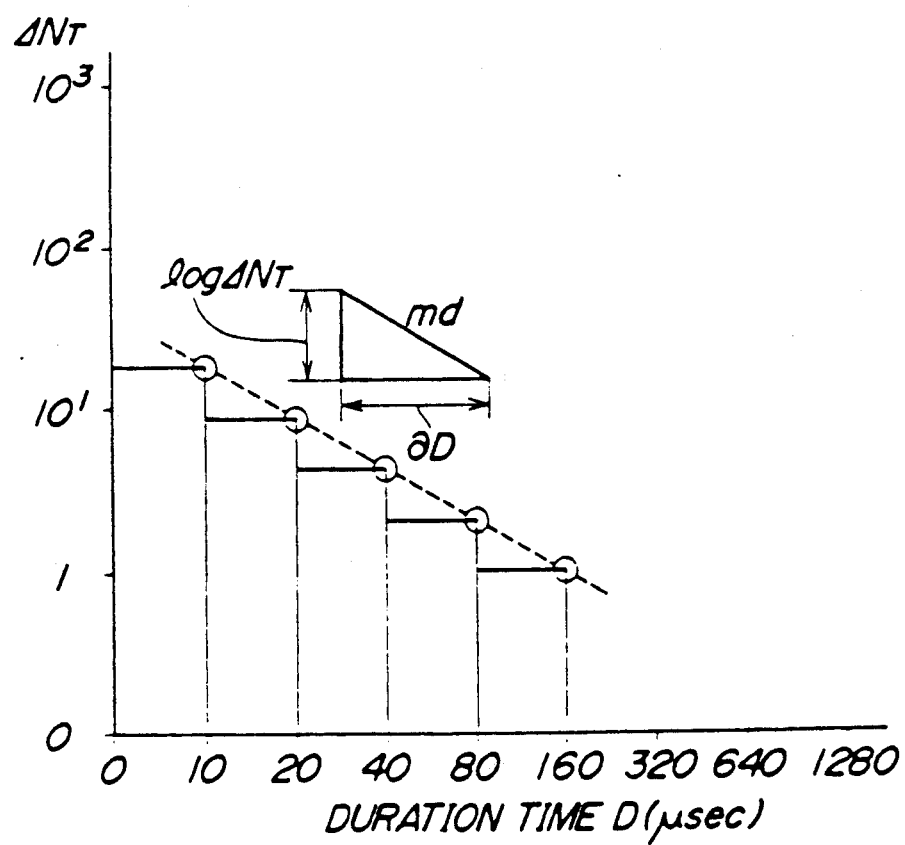
FIG. 9 is a diagram showing a duration time distribution of of the signal pulses detected during the $\Delta RT$.

In FIG. 9, if the slope of distribution of the duration time D of the signal pulses after envelope detection detected during the predetermined very small period of time ΔRT is designated by Md, the Md is expressed as follows:

$$Md = (\partial \log \Delta N_T)/\partial D$$

As the microcrack grows, the duration time D becomes longer, so that an increased number of signal pulses after envelope detection have relatively long duration times. Therefore, the slope Md of distribution of duration time D is monitored and when the slope Md exceeds a predetermined value, an alarm command signal is supplied from the CPU 36 to the alarm 39, whereby the microcrack is detected with high accuracy.

As described above, according to the other embodiments of the invention, the microcrack is detected based upon the distribution of amplitude or duration time of output signal pulses from the AE sensor 7 detected during the predetermined very small period of time ΔRT, which makes it possible to improve the accuracy of detection of the microcrack without being affected by noise.

Figure 10:
FIG. 10 is a photograph of a metal structure appearing on a cross-section of an inner ring of a bearing in which a microcrack was actually developed.

FIG. 10 is a photograph (100 magnifications) of a metal structure appearing on a cross-section of an inner ring in which a microcrack was actually detected by the apparatus according to the invention. In the photograph, the microcrack clearly appears at a location a little lower than the surface of the inner ring.

Figure 11:
FIG. 11 is a photograph of a metal structure appearing on a cross-section of a portion of another inner ring where a microcrack was actually developed.
Figure 12:
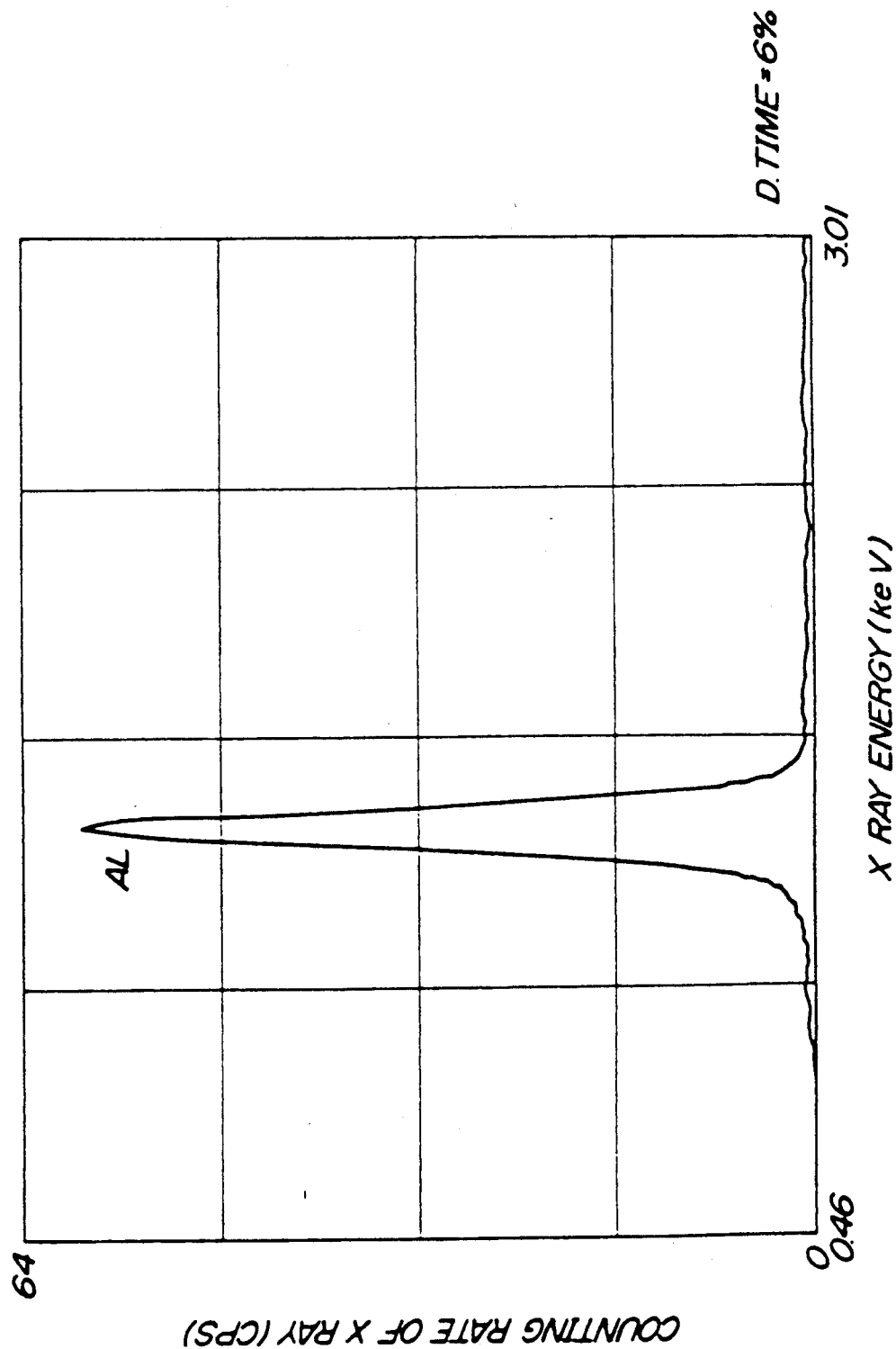
FIG. 12 is a graph showing the result of a chemical analysis of the origin of the microcrack appearing in FIG. 11 by energy distribution X ray (EDX).

FIG. 11 is a photograph (1960 magnifications) of a cross-section of the origin of a microcrack detected in another inner ring. This photograph shows details of the origin. FIG. 12 is a graph showing the result of a chemical analysis of the origin by energy distribution X ray (EDX). It can be clearly seen from this graph that aluminum (Al) is present at the origin.

What is claimed is:

1. An apparatus for detecting a crack in a bearing including a stationary element, a moving element, and a plurality of rolling elements disposed between said stationary element and said moving element at equal intervals in a direction of movement of said moving element and movable in said direction, the apparatus comprising:

crack detecting means for detecting a signal characteristic of a crack in said bearing;

a rolling element position sensor for detecting a position of said rolling elements;

a moving element position sensor for detecting a position of said moving element; and control means connected to said crack detecting means, said rolling element position sensor, and said moving element position sensor;

said control means determining, when an output signal from said crack detecting means is supplied thereto for the first time, based on at least one of position signals respectively supplied from said rolling element position sensor and said moving element position sensor, a condition of said at least one of position signals to be satisfied when said output signal from said crack detecting means is supplied to said control means the next time, monitoring said at least one of position signals thereafter, accumulating said output signal from said crack detecting means if said output signal is supplied to said control means when said at least one of position signals satisfying said condition is supplied to said control means, and determining whether or not said crack exists in said bearing based on a result of said accumulation.

2. An apparatus according to claim 1, wherein said result of said accumulation is a numerical value indicative of a number of times said output signal has been supplied to said control means accumulated by adding a predetermined numerical value to an immediately preceding numerical value accumulated, when said output signal from said crack detecting means is supplied to said control means 3. An apparatus according to claim 1, wherein said result of said accumulation is a value accumulated by adding a value corresponding to amplitude of said output signal from said crack detecting means to an immediately preceding value 4. An apparatus according to claim 2 or claim 3, wherein said control means determines that said crack exists in said bearing when said accumulated value exceeds at least one predetermined value 5. An apparatus according to claim 2 or claim 3, wherein said control means determines that said crack exists in said bearing when said accumulated value has an increase rate exceeding a predetermined value.

6. An apparatus according to claim 1, wherein said control means detects values of amplitude of said output signal from said crack detecting means for a predetermined time period, repeatedly effects said detection, determines distributions of said values of amplitude detected, and determines based on said distributions, whether or not said crack exists in said bearing.

7. An apparatus according to claim 1, wherein said control means detects duration times of said output signal from said crack detecting means for a predetermined time period, repeatedly effects said detection, determines distributions of said duration times detected, and determines based on said distributions, whether or not said crack exists in said bearing.

8. An apparatus according to claim 6 or claim 7, wherein said control means determines that said crack exists in said bearing when a slope of a curve characteristic of said distribution exceeds a predetermined value.

9. An apparatus according to any of claims 1, 2, 3, 6, or 7, including alarm generating means which generates an alarming signal when said control means determines that said crack exists in said bearing.

10. A method for detecting a crack in a bearing including a stationary element, a moving element a plurality of rolling elements disposed between said stationary element and said moving element at equal intervals in a direction of movement of said moving element and movable in said direction, and crack detecting means for detecting a signal characteristic of a crack in said bearing, the method comprising the steps of:
(1) detecting a position of said rolling elements;
(2) detecting a position of said moving element;
(3) determining, when an output signal from said crack detecting means is supplied for the first time based on at least one of position signals respectively indicative of said position of said rolling elements and said position of said moving element detected in said steps (1) and (2), a condition of said at least one of position signals to be satisfied when said output signal from said crack detecting means is supplied the next time;
(4) monitoring said at least one of position signals thereafter;
(5) accumulating said output signal from said crack detecting means if said output signal is supplied when said at least one of position signals satisfying said condition is supplied; and
(6) determining whether or not said crack exists in said bearing based on a result of said accumulation.

11. A method according to claim 10, wherein said result of said accumulation is a numerical value indicative of a number of times said output signal has been supplied accumulated by adding a predetermined numerical value to an immediately preceding numerical value accumulated, when said output signal from said crack detecting means is supplied.

12. A method according to claim 10, wherein said result of said accumulation is a value accumulated by adding a value corresponding to amplitude of said output signal from said crack detecting means to an immediately preceding value.

13. A method according to claim 11 or claim 12, wherein said step (6) comprises determining that said crack exists in said bearing when said accumulated value exceeds at least one predetermined value.

14. A method according to claim 11 or claim 12, wherein said step (6) comprises determining that said crack exists in said bearing when said accumulated value has an increase rate exceeding a predetermined value.

15. A method according to claim 10, wherein said step (5) comprises detecting values of amplitude of said output signal from said crack detecting mean for a predetermined time period, and repeatedly effecting said detection, said step (6) comprising determining distributions of said values of amplitude detected, and determining, based on said distributions, whether or not said crack exists in said bearing.

16. A method according to claim 10, wherein said step (5) comprises detecting duration times of said output signal from said crack detecting means for a predetermined time period, and repeatedly effecting said detection, said step (6) comprising determining distributions of said duration times detected, and determining, based on said distributions, whether or not said crack exists in said bearing.

17. A method according to claim 15 or claim 16, wherein said step (6) comprises determining that said crack exists in said bearing when a slope of a curve characteristic of said distribution exceeds a predetermined value.

18. A method according to any of claims 10, 11, 12, 15, or 16, including the step of:
(7) generating an alarming signal when it is determined that said crack exists in said bearing

* * * * *